United States Patent
Schmieding et al.

(12)

(10) Patent No.: US 10,729,549 B2
(45) Date of Patent: Aug. 4, 2020

(54) IMPLANTATION OF MICRONIZED ALLOGRAFT TISSUE OVER A MICROFRACTURED DEFECT

(71) Applicant: Arthrex, Inc., Naples, FL (US)

(72) Inventors: Reinhold Schmieding, Naples, FL (US); Brandon L. Roller, Naples, FL (US); David O. Shepard, Naples, FL (US); Gregory J. Karnes, Estero, FL (US); Robert Benedict, Fort Myers, FL (US); Tithi Dutta Roy, Estero, FL (US); Brian J. Cole, Chicago, IL (US); James P. Bradley, Pittsburgh, PA (US); Eric Giza, Carmichael, CA (US); James L. Cook, Columbia, MO (US); Lisa A. Fortier, Syracuse, NY (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/220,785

(22) Filed: Dec. 14, 2018

(65) Prior Publication Data
US 2019/0117403 A1 Apr. 25, 2019

Related U.S. Application Data

(62) Division of application No. 13/911,135, filed on Jun. 6, 2013, now abandoned.
(Continued)

(51) Int. Cl.
*A61F 2/30* (2006.01)
*A61L 27/36* (2006.01)
(Continued)

(52) U.S. Cl.
CPC ...... *A61F 2/30756* (2013.01); *A61L 27/3604* (2013.01); *A61L 27/3616* (2013.01);
(Continued)

(58) Field of Classification Search
CPC .................................................. A61F 2/30756
See application file for complete search history.

(56) References Cited

U.S. PATENT DOCUMENTS

| 4,551,135 A | 11/1985 | Gorman |
| 6,110,209 A | 8/2000 | Stone |

(Continued)

OTHER PUBLICATIONS

BST-CarGel®, BioSyntech, Primal Life Sciences, 2012.
(Continued)

*Primary Examiner* — Bruce E Snow
*Assistant Examiner* — Melissa A Hoban
(74) *Attorney, Agent, or Firm* — DLA Piper LLP

(57) ABSTRACT

Techniques, mixtures, mixing and delivery kits, and improved delivery instruments for implantation of micronized allograft tissue over a microfractured defect. Allograft cartilage tissue is delivered over a cartilage defect that has been debrided and microfractured, without the need for a periosteal covering or separate type of patch sewn over the top. The allograft tissue may be any micronized cartilage particulates obtained by various methods, for example, cartilage delivered in its native form, dehydrated via lyophilization, "freeze-dried," dehydrated via desiccation, or dehydrated by any other method.

19 Claims, 10 Drawing Sheets

Related U.S. Application Data

(60) Provisional application No. 61/660,351, filed on Jun. 15, 2012.

(51) Int. Cl.
*A61L 27/38* (2006.01)
*A61F 2/46* (2006.01)

(52) U.S. Cl.
CPC ......... *A61L 27/3834* (2013.01); *A61F 2/4618* (2013.01); *A61F 2002/30588* (2013.01); *A61L 27/3612* (2013.01)

(56) References Cited

U.S. PATENT DOCUMENTS

| | | | |
|---|---|---|---|
| 7,067,123 | B2 | 6/2006 | Gomes |
| 7,488,348 | B2 | 2/2009 | Truncale |
| 7,824,711 | B2 | 11/2010 | Kizer |
| 2005/0196460 | A1 | 9/2005 | Malinin |
| 2005/0288796 | A1 | 12/2005 | Awad |
| 2008/0139694 | A1 | 6/2008 | Ratcliffe |
| 2008/0220044 | A1 | 9/2008 | Semler |
| 2010/0211173 | A1 | 8/2010 | Bardos |
| 2013/0098942 | A1* | 4/2013 | Greter .................. A61J 1/2096 222/136 |

OTHER PUBLICATIONS

Gelrin C Overview, Regentis Biomaterials, 2012.
DeNovo NT (Natural Tissue) Graft, Surgical Technique, Zimmer, 2009.
"Dr. Hosea Co-Authors Study Results on New Cartilage Repair System" (Cartilage Autograft Implantation System), Am J Spors Med, vol. 39, No. 6, Abstract (Jun. 2011).
Autologous chondrocyte implantation, Wikipedia, Nov. 2008.
E. Giza, "Arthroscopic LCM Delivery for Small/Medium Sized Talus Cartilage Defects," UC Davis Health System (Nov. 29, 2010).
N. Cheng et al., "Chondrogenic Differentiation of Adipose-Derived Adult Stem Cells by a Porous Scaffold Derived from Native Articular Cartilage Extracellular Matrix", Tissue Engineering, vol. 15, No. 2, 2009, pp. 231-241.
N Chadha et al. "Porous Cartilage-Derived Matrix Scaffolds for Repair of Articular Cartilage Defects", ORS 2012; Poster No. 0735.

* cited by examiner

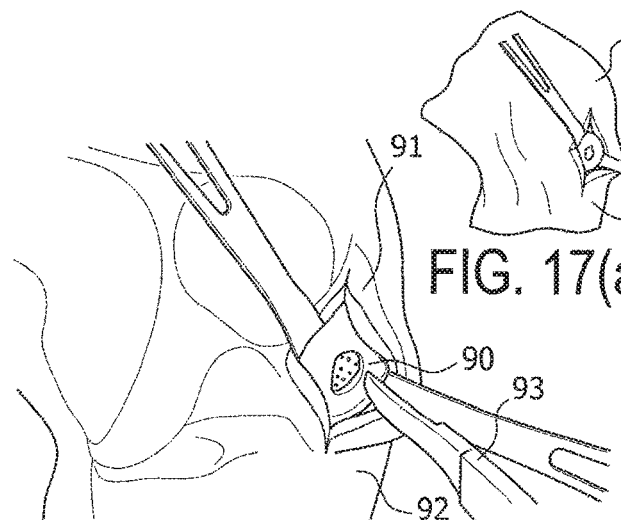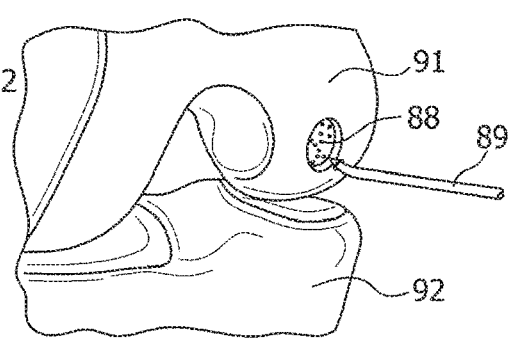
FIG. 17(a)
FIG. 17
FIG. 18
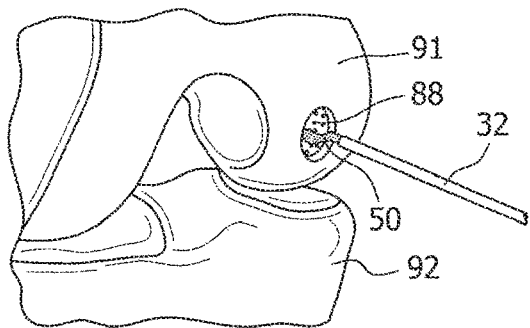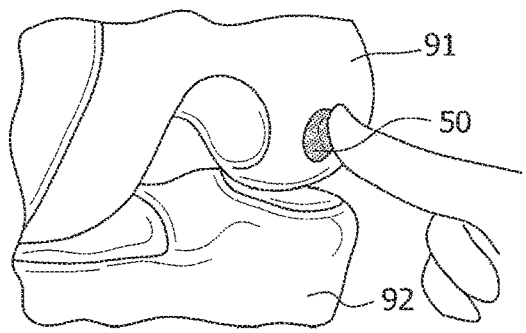
FIG. 19
FIG. 20
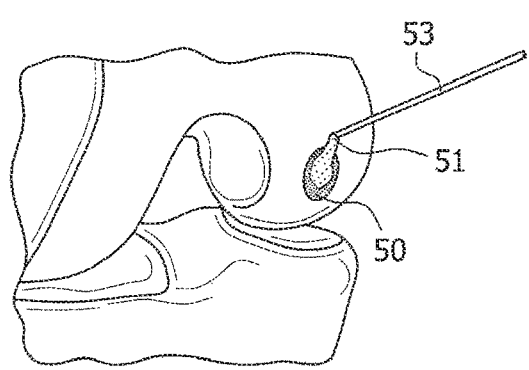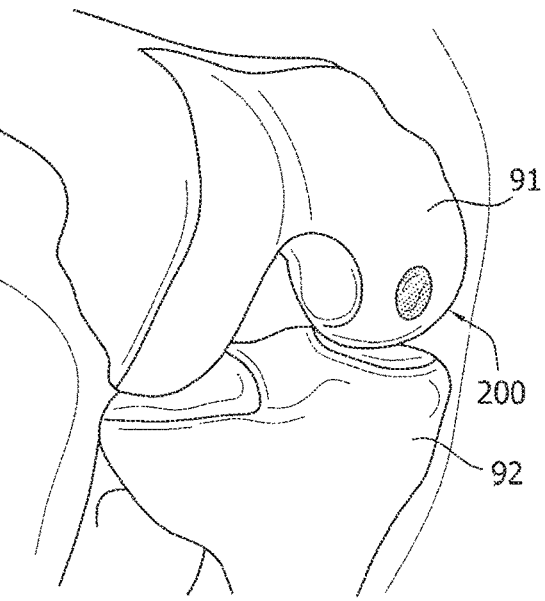
FIG. 21
FIG. 22

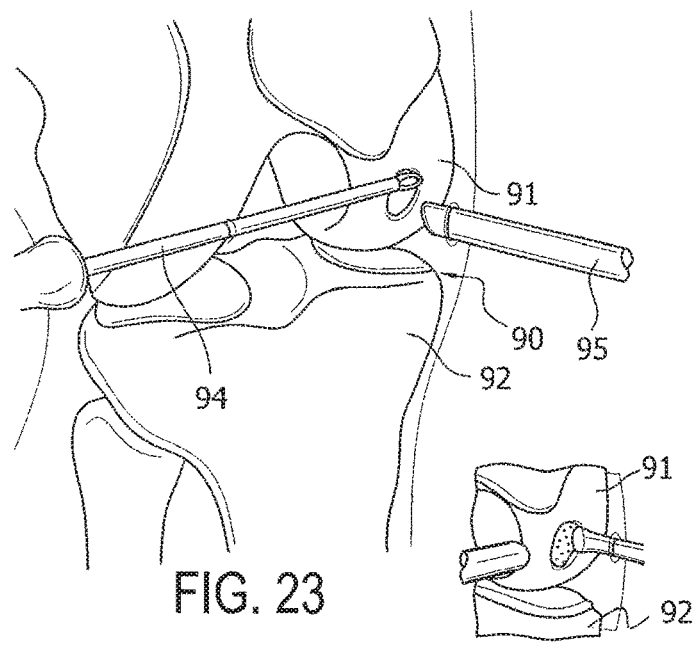
FIG. 23
FIG. 23(a)
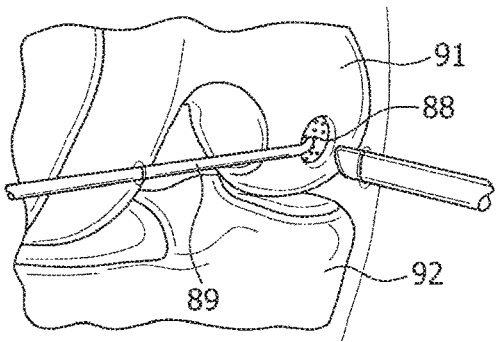
FIG. 24
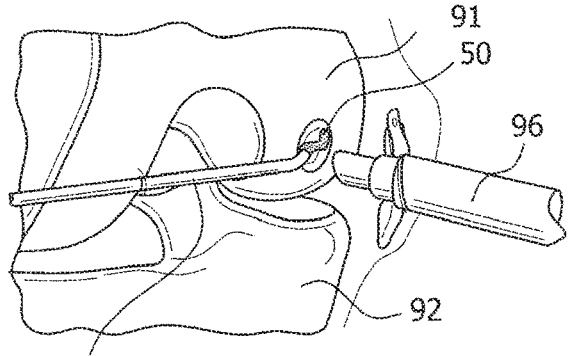
FIG. 25
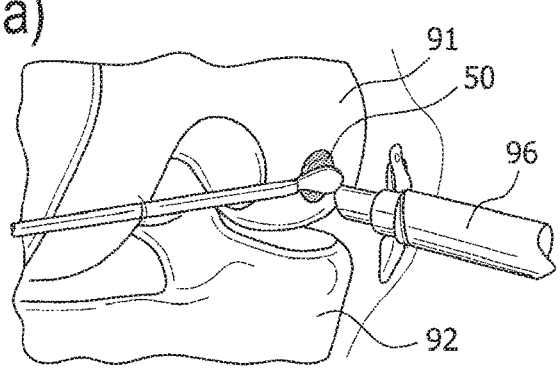
FIG. 26
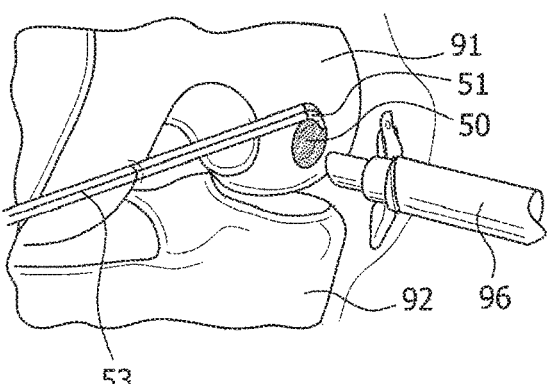
FIG. 27
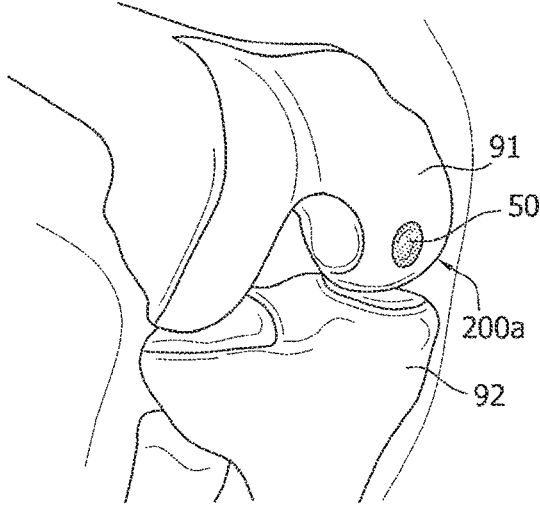
FIG. 28

IMPLANTATION OF MICRONIZED ALLOGRAFT TISSUE OVER A MICROFRACTURED DEFECT

CROSS-REFERENCE TO RELATED APPLICATIONS

This application claims the benefit of U.S. Provisional Application No. 61/660,351 filed Jun. 15, 2012, the disclosure of which is incorporated by reference in its entirety herein.

FIELD OF THE INVENTION

The present invention relates to the field of surgery and, more particularly, to improved technologies for allograft cartilage repairs.

BACKGROUND OF THE INVENTION

Articular cartilage injuries affect approximately 900,000 individuals in the United States every year. Numerous surgical interventions exist which focus on inciting cartilage repair including debridement and chondroplasty, microfracture, osteochondral allograft transplantation, and autologous chondrocyte implantation (ACI). These techniques have varying levels of success, with the ultimate goal being to generate hyaline cartilage in the defect, to recreate normal articular congruity, and to improve overall functioning, disability and health. Of these various techniques, microfracture is the most commonly utilized.

The microfracture procedure is a form of bone-marrow stimulation which enhances cartilage repair by taking advantage of the body's own healing potential. A sharp awl (i.e., a pick) is used arthroscopically through one of the arthroscopic skin portals and a mallet is used to impact the awl into the subchondral bone and thus generate bleeding from the bone. Holes are created at regular intervals until the entire defect has been addressed. The penetration of the subchondral bone allows for the communication of the osteochondral defect with mesenchymal stem cells and growth factors from the bone marrow and eventually leads to the formation of fibrocartilagenous tissue that covers the cartilage lesion.

Microfracture is typically performed by arthroscopy, after the joint is cleaned of calcified cartilage. Through use of an awl, the surgeon creates tiny fractures in the subchondral bone plate. Blood and bone marrow (which contains stem cells) seep out of the fractures, creating a blood clot over the defect. The stem cells from the bone marrow and from the underlying subchondral bone interact with the clot and use this as the initial scaffold to begin the process of cellular differentiation into fibrocartilage or cartilage-building cells. The microfractures are treated as an injury by the body, which is why the surgery results in new, replacement tissue. The procedure is effective in gaining a combination of fibrocartilage and hyaline cartilage (which are not formed from an osteochondritis dissecan (OC) defect alone).

Although good results have been achieved with microfracture treatments, some studies have concluded that, while microfracture provides effective short-term functional improvement of knee function, there is insufficient data on its long-term results. Additional shortcomings of the technique include limited hyaline repair tissue, variable repair cartilage volume, and possible functional deterioration over time.

A recent technology used to augment the microfracture technique is through the use of an allograft extracellular matrix. BioCartilage® is an example of desiccated micronized cartilage extracellular matrix tissue allograft that has been developed for ICRS grade III or greater articular cartilage lesions in conjunction with microfracture.

BioCartilage® is developed from allograft cartilage that has been dehydrated and micronized. BioCartilage® contains the extracellular matrix that is native to articular cartilage including key components such as type II collagen, proteoglycans, and additional cartilaginous growth factors. The principle of BioCartilage® is to serve as a scaffold over a microfractured defect providing a tissue network that can potentially signal autologous cellular interactions and improve the degree and quality of tissue healing within a properly prepared articular cartilage defect.

This allograft tissue is combined with platelet-rich plasma and the resultant solution is added to a microfractured chondral lesion and "fixed" with a fibrin coverage. The addition of platelet-rich plasma (PRP) to the dessicated BioCartilage® scaffold is considered a beneficial addition due to the anabolic and anti-inflammatory factors associated with PRP. The added fibrin content in PRP provides additional structure to the final matrix pre and post implantation.

A need exists for techniques that allow delivery of allograft cartilage tissue over a cartilage defect that has been debrided and microfractured, without the need for a periosteal covering or separate type of patch sewn over the top. Also needed are methods and special delivery instruments for rebuilding a defective cartilage in difficult-to-reach areas such as the ankle. An augmented microfracture procedure that addresses sub-chondral lesions is also needed.

BRIEF SUMMARY OF THE INVENTION

The present invention provides techniques, mixtures, mixing and delivery kits, and improved delivery instrumentation for implantation of micronized allograft tissue over a microfractured defect. Micronized allograft tissue is delivered over a cartilage defect that has been debrided and microfractured, without the need for a periosteal covering or separate type of patch sewn over the top.

The allograft tissue may consist of any micronized cartilage particulates obtained by various methods, for example, cartilage delivered in its native form, dehydrated via lyophilization, "freeze-dried," dehydrated via desiccation, or dehydrated by any other method. The micronized cartilage particulates may have a size of about 0-300 microns.

The methods of the present invention use allograft material over a cartilage defect that has been prepared by microfracture surgery. The mixture of the allograft material has a paste-like consistency so that it can be conformed to any defect size or shape, including the ability of the paste-like mixture to be delivered during an open procedure or arthroscopically. A fibrin adhesive may be utilized, preferably more as a covering and not throughout the product. The method of the present invention also provides formation of micronized particles via the process of desiccation instead of lyophilization.

Other features and advantages of the present invention will become apparent from the following description of the invention.

BRIEF DESCRIPTION OF THE DRAWINGS

FIGS. 17-22 illustrate subsequent steps of a method of delivering the micronized allograft tissue of FIG. 12 over a microfractured defect (an exemplary microfractured knee defect) according to an exemplary embodiment of the present invention.

FIGS. 23-28 illustrate subsequent steps of a method of delivering the micronized allograft tissue of FIG. 12 over a microfractured defect (an exemplary microfractured knee defect) according to another exemplary embodiment of the present invention.

DETAILED DESCRIPTION OF THE INVENTION

Figure 1:
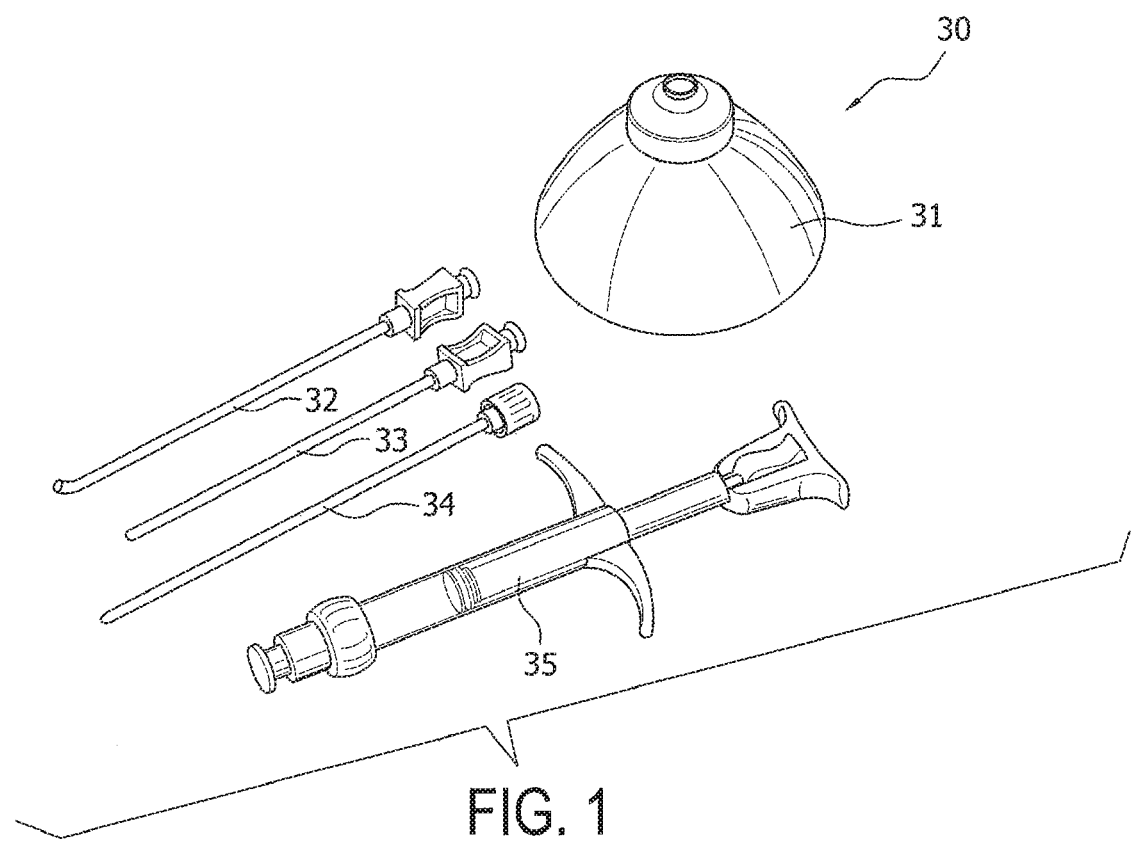
FIGS. 1-12 illustrate instruments, mixing kits and methods of forming micronized allograft tissue according to an exemplary embodiment of the present invention.

The present invention provides mixing and delivery techniques for micronized allograft tissue over a microfractured defect. The present invention also provides techniques for implantation of such micronized allograft tissue at a microfracture site.

Allograft tissue is delivered over a cartilage defect that has been debrided and microfractured without the need for a periosteal covering or separate type of patch sewn over the top. The allograft tissue may be allograft cartilage in the form of micronized cartilage particulates which may be cartilage delivered in its native form, dehydrated via lyophilization, dehydrated via desiccation, or dehydrated by any other method, among others. The micronized cartilage particulates may have a size of about 0-300 microns.

In an exemplary embodiment only and as detailed below, cartilage with particles of about 0-300 microns is employed to form a moldable allograft paste (mixture or composition). Preferably, the moldable allograft paste comprises cartilage in the form of morsellized, freeze-dried and/or desiccated cartilage. Cartilage (in the form of morsellized, freeze-dried and/or desiccated cartilage) may be processed by a tissue bank similar to the BioCartilage® process for hyaline cartilage. The sterile, freeze-dried and/or desiccated product is mixed (by the orthopedic surgeon, for example) at the time of surgery with autologous blood or a biologic equivalent to create a moldable allograft paste that can be delivered (by injection, for example) at the microfracture site.

The present invention also provides methods of tissue repairs of an articular cartilage defect with microfracture and micronized allograft tissue. An exemplary method of providing/implanting micronized allograft tissue over a microfractured defect according to an exemplary embodiment of the present invention comprises inter alia the steps of: (i) conducting microfracture surgery to provide a microfracture site at an articular cartilage defect; (ii) mixing allograft tissue (cartilage) micronized into particles with a size of about 0-300 μm with an autologous blood product (whole blood, platelet-rich plasma, autologous conditioned plasma, bone marrow, or stems cells, among others) in a specially-designed mixing syringe, to obtain a micronized allograft mixture having a paste-like consistency that can be injected through a needle or small cannula; and (iii) delivering the micronized allograft mixture at the microfracture site (through either an open procedure or an arthroscopic procedure).

The present invention also provides methods of preparing a micronized cartilage mixture. An exemplary method comprises inter alia the steps of: (i) placing about 1.0 cc of micronized cartilage (for example, desiccated articular cartilage) into a custom 3 cc syringe; (ii) using a second syringe which contains about 1.0 cc of an autologous blood solution and injecting it into the custom syringe (in a 1:1 ratio); and (iii) mixing the autologous blood solution with the micronized cartilage in the custom syringe by using a mixing element which is built into the custom syringe, to mix the two components/substances together to create a resulting mixture with a paste-like consistency. The method may further comprise the step of providing instruments (needles) having curved or straight configurations (such as a Tuohy-style delivery needle), particularly for defects in the ankle which are more difficult to reach. For example, a curved needle (such as, a 100 Tuohy needle) may be applied to the end of the syringe containing the micronized cartilage paste, to deliver the paste to the microfracture defect.

Referring now to the drawings, where like elements are designated by like reference numerals, FIGS. 1-16 illustrate various instruments, mixing and delivery kits, and methods of forming micronized allograft tissue mixtures (having a paste-like consistency) to be delivered over a microfractured defect according to the present invention. FIGS. 17-34 illustrate various methods of delivering micronized allograft over exemplary microfractured defects according to the present invention.

FIG. 1 illustrates a mixing and delivery kit 30 employed for obtaining an exemplary micronized allograft mixture 50 of the present invention. Mixing and delivery kit 30 includes a mixing syringe 35 and cap 39 (FIG. 2), a first needle 32 (which may be a curved needle such as a curved delivery needle like a Tuohy delivery needle) and a second needle 33 (which may be a straight needle), and an obturator 34. A funnel 31 is also shown in FIG. 1 and may be optionally included as part of mixing and delivery kit 30. Mixing and delivery kit 30 may optionally include additional needles, for example, additional straight and/or curved needles, to aid in the delivery of the micronized allograft mixture 50 at the defect site.

Figure 2:
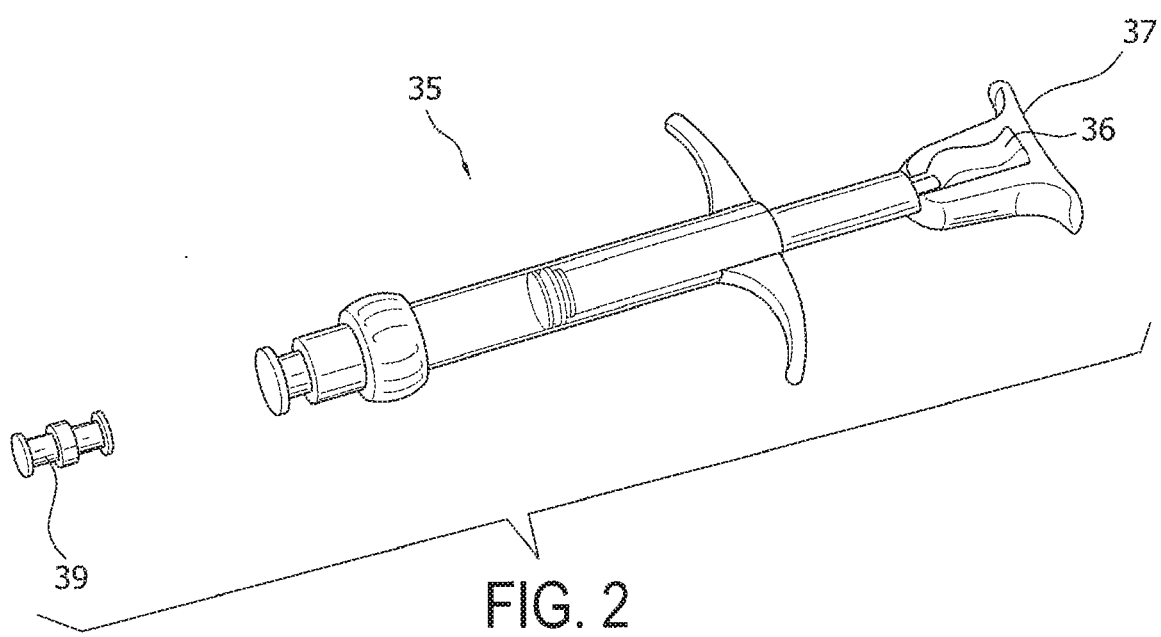

FIG. 2 illustrates an enlarged view of the special mixing syringe 35 of the present invention which is employed for the mixing/formation of micronized allograft mixture 50 (paste 50) of the present invention. Syringe 35 is a modified conventional syringe provided with a pushrod 37 that is designed and configured to unsnap from (and snap back into) a mixing element 36 (mixing rod 36), to allow components that form micronized allograft mixture 50 to mix together and then to allow the formed mixture 50 to be delivered at the surgical site (i.e., microfracture site which may be part of any articular cartilage surface, for example, a knee, an ankle, a foot, a shoulder, a hand, a wrist, an elbow, or a hip, among others), as detailed below.

FIGS. 3-12 illustrate subsequent steps of an exemplary technique of forming micronized allograft mixture 50 (paste 50) which is part of delivery system 100 (FIGS. 9 and 12) of the present invention.

Figure 3:
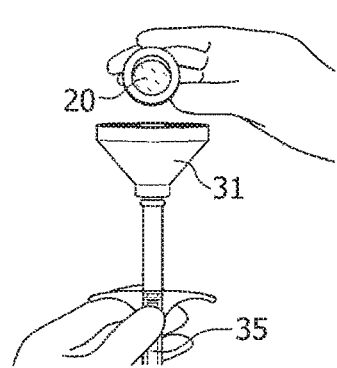

FIG. 3: Remove the syringe cap 39 and snap on the funnel 31 to the end of the syringe 35. Make sure the plunger is at the end of the syringe 35, then empty micronized allograft 20 (for example, micronized cartilage 20) from its container into the funnel 31.

Micronized allograft 20 is preferably any micronized cartilage with particles/particulates obtained by various methods, for example, cartilage delivered in its native form, dehydrated via lyophilization, "freeze-dried," dehydrated via desiccation, or dehydrated by any other method. The size of the particles forming the micronized allograft 20 may be of about 0-300 microns, to allow the micronized particles to mix well with the autologous blood product and form the resulting micronized allograft mixture 50 (paste 50).

In an exemplary-only embodiment, the micronized allograft 20 is BioCartilage®, sold by Arthrex, Inc. (Naples, Fla.), which consists essentially of allograft cartilage that has been dehydrated and micronized. BioCartilage® contains the extracellular matrix that is native to articular cartilage including key components such as type II collagen, proteoglycans, and additional cartilaginous growth factors. The principle of BioCartilage® is to serve as a scaffold over a defect providing a tissue network that can potentially signal autologous cellular interactions and improve the degree and quality of tissue healing within a properly prepared cartilage defect.

Figure 4:
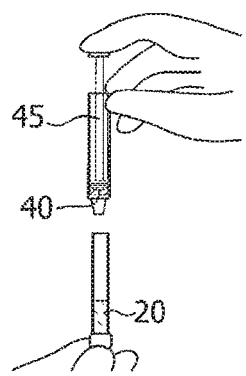
Figure 4A:
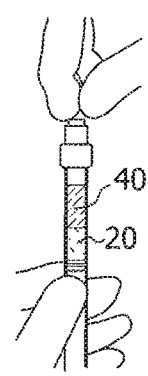

FIG. 4: Remove the funnel 31 and dispense an equivalent amount of autologous blood solution 40 (from a second syringe or container 45) as the micronized allograft 20 into the mixing syringe 35 (about 1:1 ratio). Twist on the syringe cap and luer cap.

Figure 5:
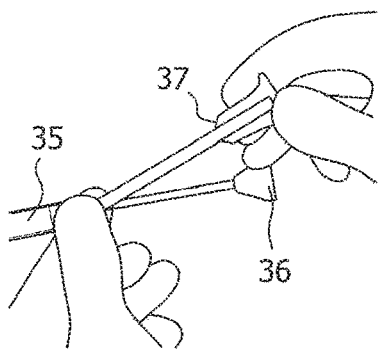

FIG. 5: Unsnap (disengage) the pushrod 37 from the mixing element 36 by pressing on the tip of the mixing element 36 with counter pressure on the tip of the pushrod 37.

Figure 6:
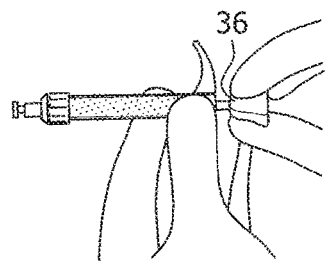

FIG. 6: To mix the micronized allograft 20 and autologous blood solution 40, push and pull the mixing element 36 back and forth while rotating it in a repeated left-to-right motion. Continue until thoroughly mixed to form micronized allograft mixture 50.

Figure 7:
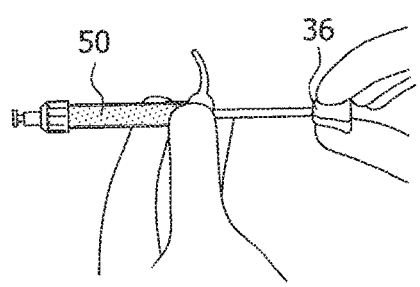

FIG. 7: Pull back the mixing element 36 to bring it back to its starting position.

Figure 8:
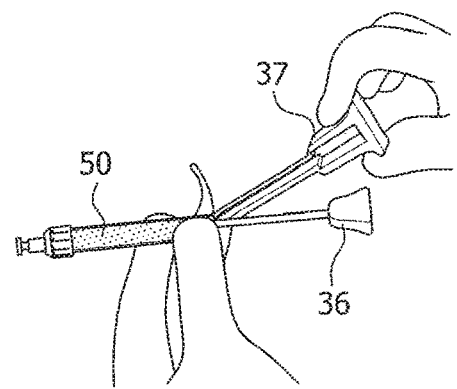

FIG. 8: Snap (engage) the pushrod 37 back onto the mixing element 36.

Figure 9:
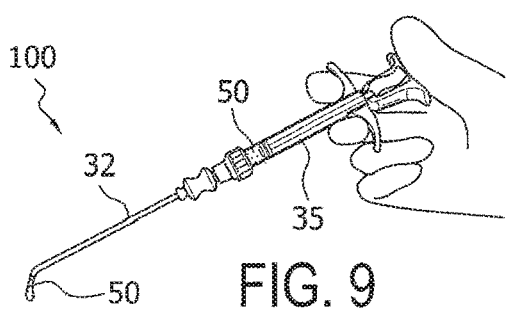

FIG. 9: Apply either the straight needle 33 (for example, an 11-gauge straight needle) or the curved needle 32 (for example, a Tuohy delivery needle) to form delivery system 100 and dispense the micronized allograft mixture 50 out of the mixing syringe 35.

Figure 10:
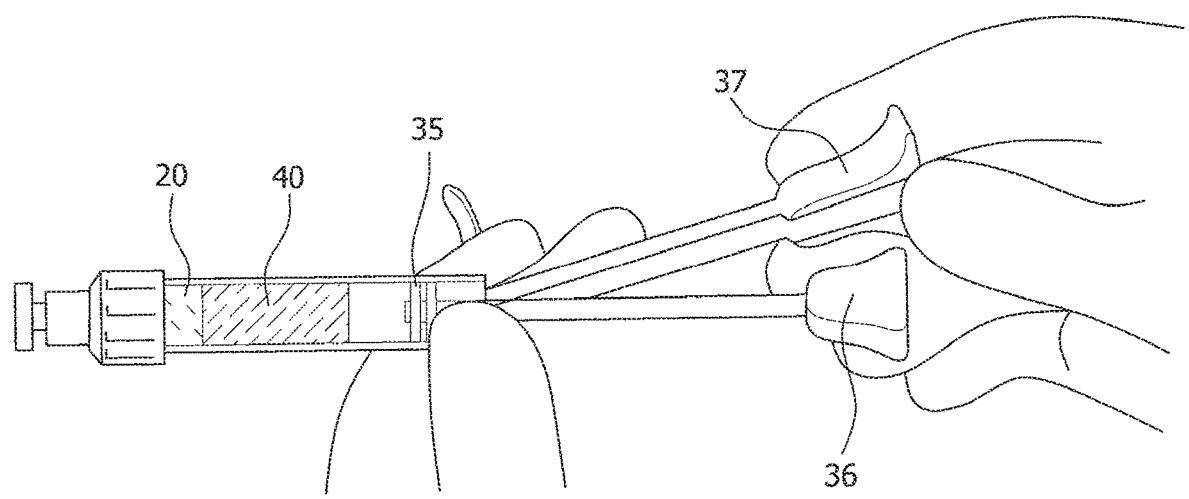
Figure 11:
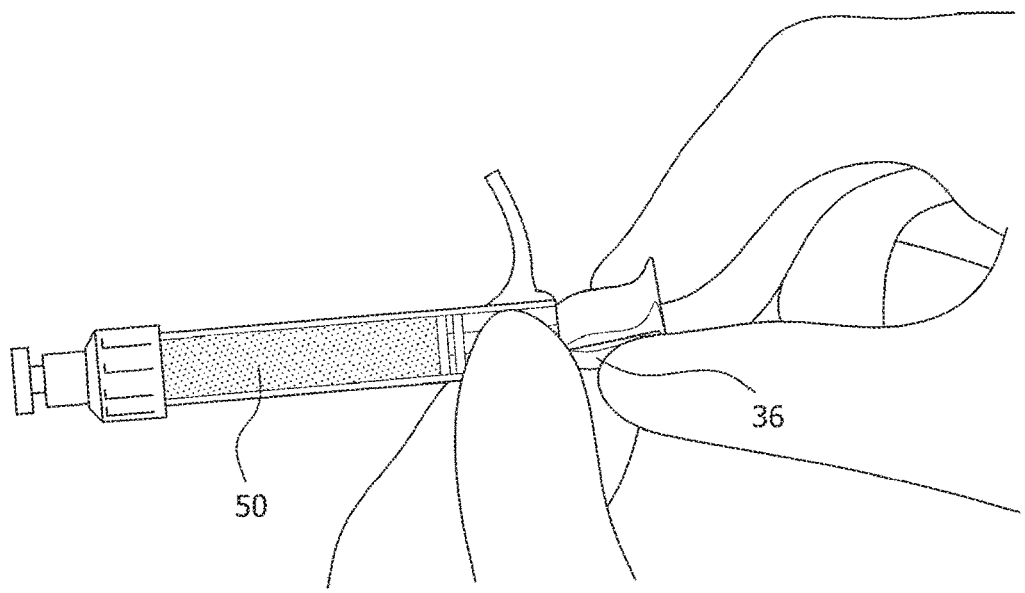
Figure 12:
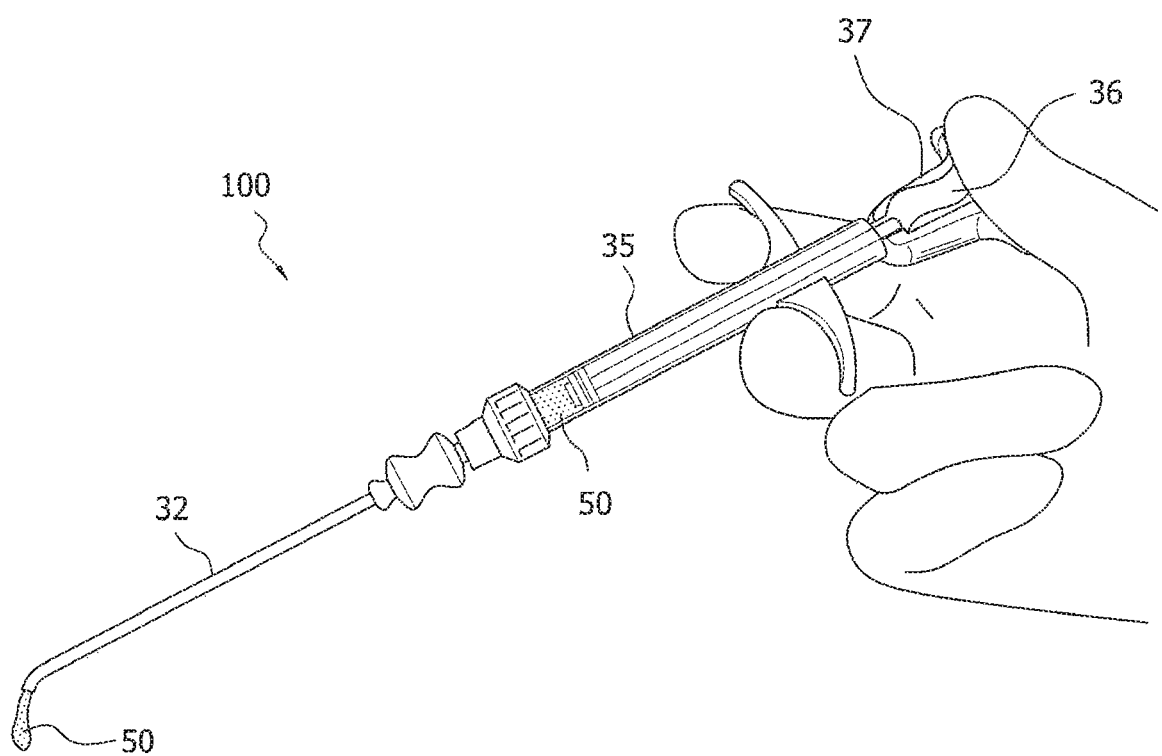
Figure 13:
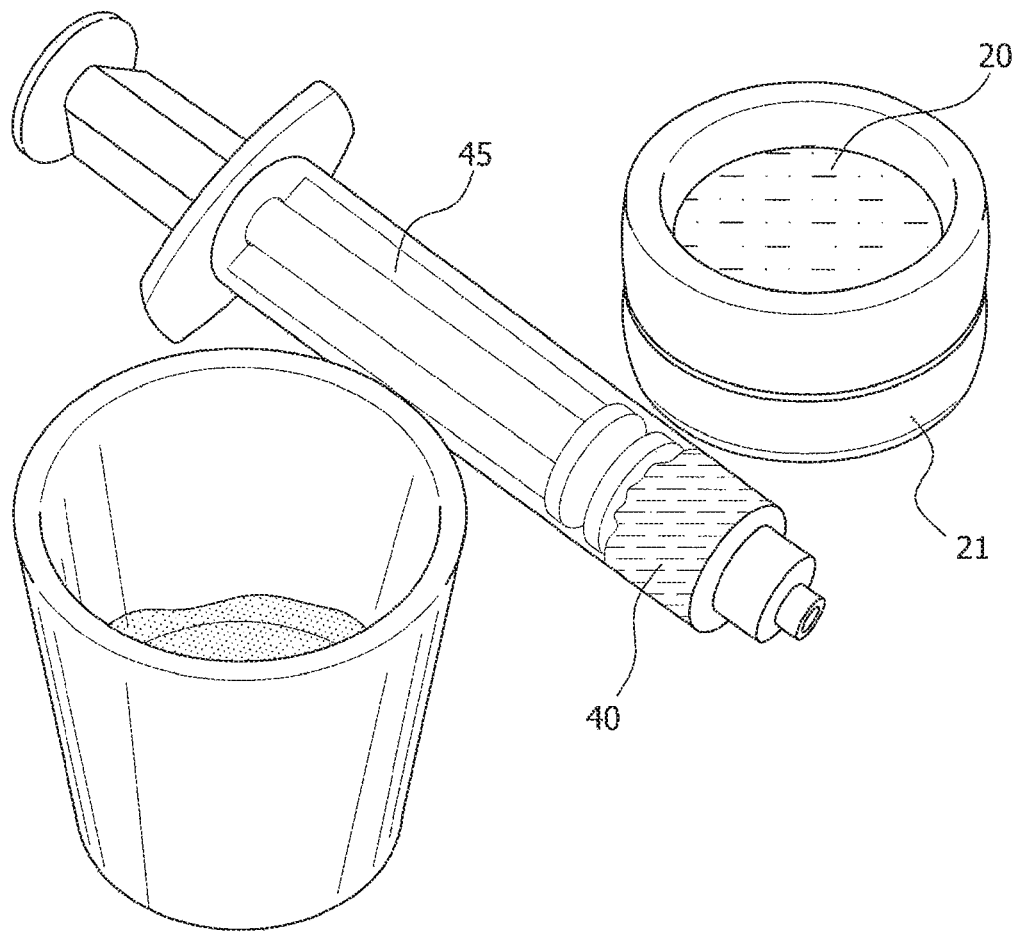
FIGS. 13-16 illustrate instruments, mixing kits and methods of forming micronized allograft tissue according to another exemplary embodiment of the present invention.
Figure 14:
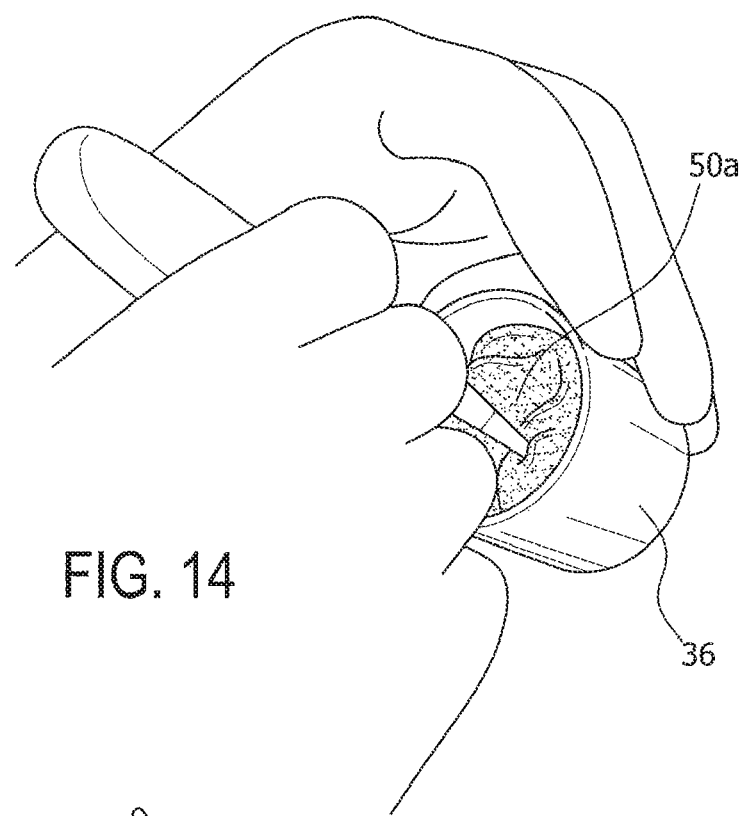

FIG. 10 illustrates an enlarged view of the special syringe 35 of the present invention with the pushrod 37 engaging/disengaging the mixing element 36 to allow mixing of the micronized allograft tissue 20 with the autologous blood solution 40 in the syringe 35. FIG. 11 illustrates how a linear motion (back and forth) and/or a rotating motion (left to right and/or vice-versa) of the mixing element 36 facilitates the mixing of the micronized allograft 20 with the autologous blood solution 40. FIG. 12 illustrates an enlarged view of the delivery system 100 of FIG. 9, showing part of the micronized allograft mixture 50 exiting needle 32 attached to the special syringe 35.

Figure 15:
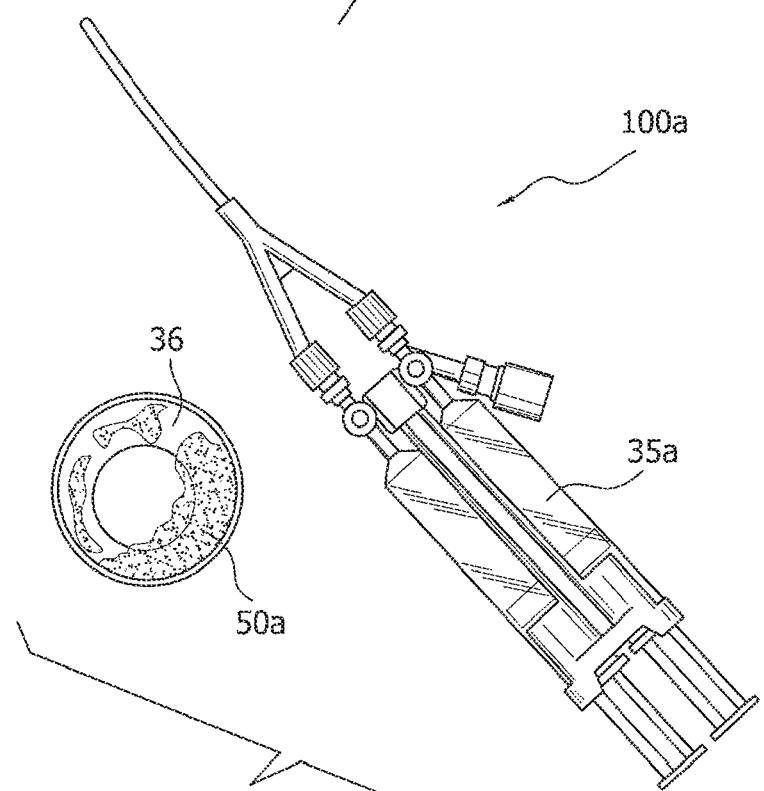
Figure 16:

FIGS. 13-16 illustrate yet another embodiment of mixing and delivery system 100a (FIG. 15) wherein autologous blood solution 40 (from a syringe or container 45) is provided in contact with micronized allograft 20 of container 21. The two components are provided in about 1:1 ratio in open container 36 and mixed by hand to obtain micronized allograft mixture 50a (paste 50a) shown in FIGS. 14-16. A special dual syringe delivery system 35a may be employed to provide/deliver the paste 50a to a microfracture site (FIG. 15). Alternatively, the paste 50a may be delivered by the surgeon to the surgical site using a hand, a dispenser, or any sterile spatula.

FIGS. 17-22 illustrate a micronized cartilage knee surgical technique according to an exemplary embodiment of the present invention. FIGS. 17-22 illustrate femur 91, tibia 92 and surgical site 90 containing an articular cartilage defect to be repaired according to the present invention.

FIGS. 17 and 17(*a*): Debride the articular cartilage defect 90 to a stable border with about perpendicular margins. A scalpel 93 or cutting instrument 93 may be used to create the vertical margins and a curette can be used to debride the calcified cartilage layer at the base of the defect. When evaluating a cartilage defect and preparing it, care must be taken to debride the cartilage to a healthy cartilaginous border. In addition, 90° margins should be created around the periphery of the defect to help with containment of the product. The calcified cartilage layer needs to be removed from the base of the defect just like when performing a microfracture procedure (unlike the ACI procedures).

FIG. 18: Perform bone marrow stimulation using standard microfracture surgery to form several perforations in the subchondral bone plate of microfracture site 88. A power pick 89 may be used to perform this procedure while applying irrigation fluid to avoid thermal necrosis. The microfracture procedure is performed through the subchondral plate which allows marrow elements to incorporate into the implanted allograft material.

FIG. 19: Dry the defect thoroughly. The defect is dried with gauze sponges or pledgets, for example, before implantation of the allograft material.

Before implanting the allograft material 50, a drop or two of fibrin adhesive can be applied to the corners of the base of the defect to provide additional adhesive properties between the bone bed and allograft material. It is preferred not to use fibrin adhesive when possible, as to not occlude the microfracture holes that were created.

The allograft cartilage 20 is micronized into particles with a small enough size (of about 0-300 microns) so that when it is mixed with a fluid such as an autologous blood product it has a paste-like consistency that can be injected through a needle or small cannula. The autologous blood product may be blood (whole blood), autologous conditioned plasma, platelet-rich plasma, bone marrow (for example, bone marrow concentrate or bone marrow aspirate), stem cells (concentrated or expanded stem cells), or combinations thereof. The allograft cartilage 20 can be provided in a dehydrated state via a desiccation process or hypothermic dehydration process instead of lyophilization of the material.

The micronized cartilage 20 is then mixed with an autologous blood solution 40 (1:1 ratio) within the mixing syringe to form micronized allograft mixture 50 (cartilage paste 50). After mixing the micronized cartilage tissue 20 with the autologous blood solution 40, the cartilage mixture 50 is applied at the defect 88 with exemplary delivery system 100.

As detailed above, the mixture of the allograft cartilage with the autologous blood product may take place within a closed mixing system to prevent the material from drying out when exposed to air. This also helps to provide a very consistent and repeatable mixture of the two products. The allograft/autologous blood product is delivered to the defect directly for open procedures, or through a needle or cannula for arthroscopic procedures.

As also detailed above, a straight needle or cannula may be used to deliver the mixture. For example, the straight needle/cannula can be inserted through the AM portal arthroscopically for a medial femoral condyle defect. The needle/cannula allows for delivery of the mixture directly into the defect. Alternatively, a Tuohy style needle 32 (FIG. 19) or cannula can also be used to deliver the mixture. For example, the Tuohy style needle/cannula can be inserted through the AL portal arthroscopically for a medial femoral condyle defect for cross portal delivery of the mixture or it can be used in the same fashion as the straight needle/cannula. The Tuohy shape is particularly useful for the talar lesions of the ankle because it allows for delivery into the defect much more easily than a straight needle would be able to provide.

After delivery of the allograft/autologous blood product mixture to the defect, the mixture is smoothed out over the defect so that it is flush or slightly recessed in comparison to the surrounding cartilage borders.

FIG. 20: Smooth out the cartilage mixture 50 within the defect 88. Ensure that the cartilage mixture 50 is slightly recessed when compared to the surrounding articular cartilage.

The mixture is compressed with manual pressure during open procedures. For arthroscopic procedures, a tamp can be used to provide compressive pressure directly, or an articulating elevator can be used to provide compressive pressure from the cross portal position when treating defects in the knee. For defects in the talus (and as detailed below), an elevator can be used to provide compression.

Alternatively, a metal template (which may be selected from a plurality of metal templates that match the curvature of the knee, similar to a uni-knee tamp) may be used to apply compression against the defect evenly before a fibrin glue is applied and after the fibrin glue sets up. This would help ensure the defect is filled and shaped to match the curvature of the rest of the condyle.

After compressing the mixture, additional amounts of the mixture can be delivered and impacted until the final implant is either flush or slightly recessed with respect to the surrounding cartilage borders. After delivery of the implant, a fibrin adhesive is applied over the top of the implant. The fibrin adhesive provides a smooth barrier over the implanted material. The fibrin adhesive is allowed to dry before deflating the tourniquet.

FIG. 21: Apply fibrin 51 over the top of the cartilage mixture 50. Use enough to cover the defect, but prevent over-usage as this will cause the construct to sit proud in the joint. Use of a dual lumen applicator tip 53 is recommended to apply the fibrin 51 in order to prevent activation and clogging of the fibrin 51 within the needle. Do not manipulate for 5 minutes after application. The knee may be gently ranged before closure to assure cartilage mixture 50 adherence.

FIG. 22: At the completion of surgery and repair 200, a knee immobilizer locked in extension is placed and the patient is made non-weight bearing or protected weight bearing as determined by defect location with delayed onset of range-of-motion for up to one week postoperatively. Standard rehabilitation protocols used for the tibiofemoral and patellofemoral joint may then be implemented.

FIGS. 23-28 illustrate another exemplary embodiment of a micronized cartilage knee arthrotomy surgical technique according to the present invention:

FIGS. 23 and 23(a): Debride the articular defect to a stable border with perpendicular margins. A Ring curette 94 and Cobb elevator 95 can be used to create the vertical margins and debride the calcified cartilage layer at the base of the defect 90.

FIG. 24: Perform bone marrow stimulation using a power pick 89 for microfracture formation to form microfracture site 88. After microfracture, ensure the use of a tourniquet, aspirate the arthroscopic fluid and dry the cartilage defect with pledgets.

FIG. 25: A Gemini cannula 96 is utilized in the portal that resides over the defect 88. Apply distraction of the soft tissue with the cannula 96 to improve visualization of the defect. The cartilage mixture 50 can be applied over the defect 88 with a Tuohy delivery needle 32 of delivery and mixing system 100.

FIG. 26: A paddle elevator 97 (for example, an articulating paddle elevator 97) can be used to smooth out the cartilage mixture 50 within the defect so that it remains slightly recessed to the surrounding cartilage.

FIG. 27: Apply a light layer of fibrin 51 over the cartilage mixture 50 through a dual lumen applicator tip 53; prevent over usage as this will cause the construct to sit proud. If a single lumen needle/cannula is used, this will lead to premature activation of the fibrin. Do not manipulate for 5 minutes after application. The knee may be gently ranged before closure to assure cartilage mixture 50 adherence and completion of surgery and final repair 200a (FIG. 28).

FIGS. 29-34 illustrate an exemplary ankle arthroscopic surgical technique according to another embodiment of the present invention.

Figure 29:
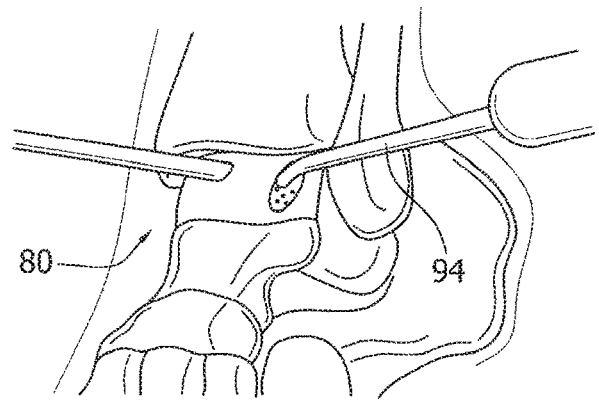
FIGS. 29-34 illustrate subsequent steps of a method of delivering the micronized allograft tissue of FIG. 12 over a microfractured defect (an exemplary microfractured ankle defect) according to another exemplary embodiment of the present invention.
Figure 29A:
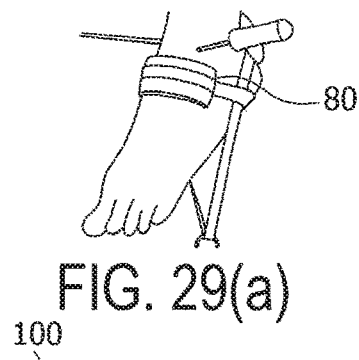

FIGS. 29 and 29(a): Under tourniquet control, apply about 4 mm of distraction to the tibiotalar joint 80. Debride the articular cartilage defect to create stable margins. A Ring Curette 94 can be used to create vertical margins and debride the base.

Figure 30:
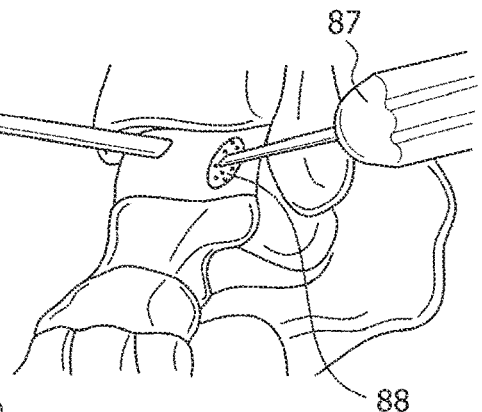

FIG. 30: Perform bone marrow stimulation utilizing a microfracture awl 87 to form microfracture site 88. Aspirate all arthroscopic fluid and dry the cartilage defect with pledgets.

Figure 31:
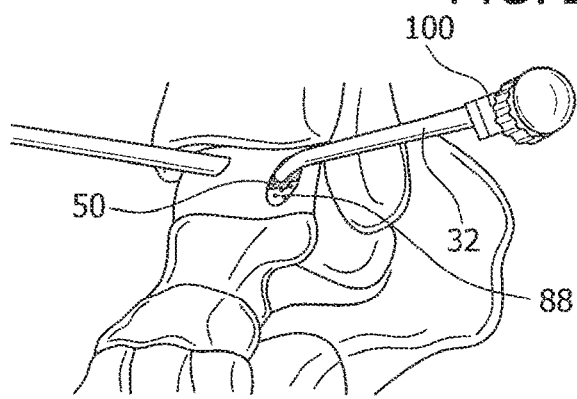

FIG. 31: After mixing the micronized cartilage tissue 20 with an autologous blood solution 40 (1:1 ratio) within the mixing syringe 35 to form cartilage mixture 50, apply the mixture 50 into the defect 88 utilizing the Tuohy Delivery Needle 32.

Figure 32:
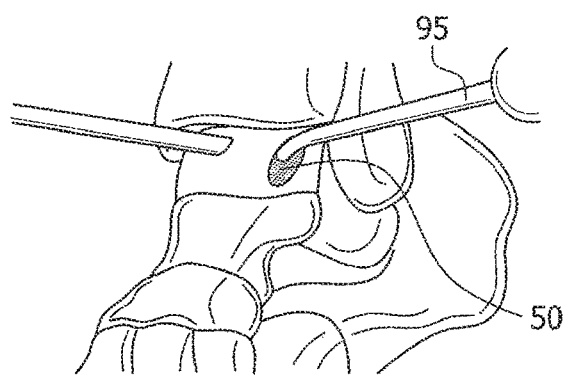

FIG. 32: A Cobb Elevator 95 can be used to smooth out the cartilage mixture 50 within the defect. Ensure that the cartilage mixture 50 remains slightly recessed when compared to the surrounding cartilage.

Figure 33:
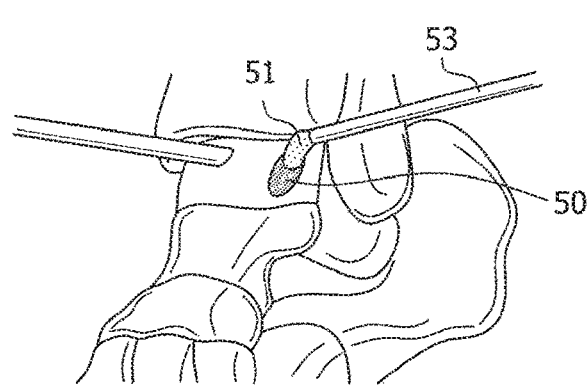

FIG. 33: Apply fibrin 51 over the cartilage mixture 50 through a dual lumen applicator tip 53. Avoid applying too much fibrin 51 to prevent the construct from sitting proud.

Figure 34:
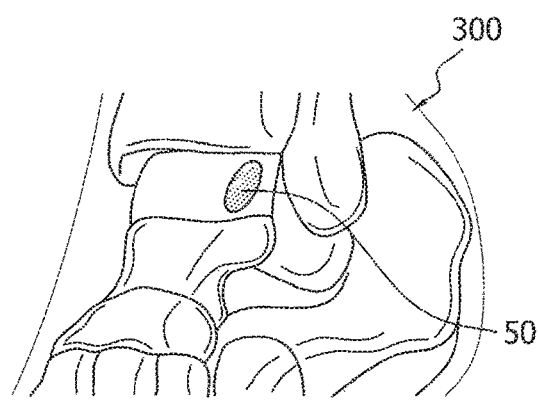

FIG. 34: At the completion of surgery, the ankle is immobilized in neutral position and the patient is made non-weight bearing. Standard rehabilitation protocols following microfracture surgery may then be implemented.

The micronized cartilage mixture 50, 50a of the present invention may optionally comprise additional components such as proteins, growth factors or chemicals that may be provided within the mixtures. The autologous blood product may be blood (whole blood), plasma, autologous conditioned plasma, platelet-rich plasma, bone marrow, bone marrow aspirate, bone marrow concentrate, stem cells such as concentrated or expanded stem cells (derived from a variety of sources), or any combinations of these products.

In accordance with exemplary-only embodiments, the mixtures may be obtained to additionally comprise components such as growth factors, additional antiseptic chemicals and/or antibiotics and/or electrolytes, or hormones or site-specific hybrid proteins (that promote or enhance the wound healing effectiveness of the growth factors), or glue such as fibrin glue and/or adhesives, among others.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

We claim:

1. A method comprising:
   (a) placing a micronized cartilage mixture comprising (i) micronized allograft cartilage particles above 0 to about 300 microns, (ii) type II collagen, (iii) proteoglycans, (iv) cartilaginous growth factors into a first syringe, wherein the first syringe comprises a tube and a plunger that fits in the tube, the plunger being formed of a pushrod and a mixing element attached to the pushrod, the pushrod fitting into the mixing element and being designed to unsnap from the mixing element and snap back into the mixing element;
   (b) providing a second syringe or second container containing platelet rich plasma and injecting the platelet rich plasma into the first syringe;
   (c) removing the pushrod from the mixing element and moving the mixing element in at least one direction to mix the micronized allograft tissue particles with the platelet rich plasma to create a micronized allograft mixture with a paste consistency;
   (d) applying a needle or small cannula to the first syringe;
   (e) debriding an articular cartilage defect site to form a stable border;
   (f) forming several perforations in a subchondral bone plate at the base of the articular cartilage defect site using microfracture techniques to form a microfracture site; and
   (g) delivering a graft comprising the micronized allograft mixture with a paste consistency directly at the microfracture site, such that the micronized allograft mixture fills the articular cartilage defect site.

2. The method of claim 1, wherein the micronized allograft cartilage particles are morselized, freeze-dried, or desiccated cartilage.

3. The method of claim 1, further comprising the step of applying a layer of fibrin over the micronized allograft mixture at the microfracture site.

4. The method of claim 1, wherein the micronized allograft cartilage particles are desiccated cartilage particles.

5. The method of claim 1, wherein the micronized allograft mixture consists essentially of micronized allograft tissue particles, type II collagen, proteoglycans, cartilaginous growth factors, and platelet rich plasma.

6. The method of claim 1, wherein the micronized allograft mixture further comprises bone marrow aspirate, bone marrow concentrate, or stem cells.

7. The method of claim 1, wherein the micronized allograft mixture further comprises growth factors, antiseptics, antibiotics, electrolytes, or stem cells.

8. The method of claim 1, wherein the microfracture site is part of a cartilage surface.

9. The method of claim 8, wherein the microfracture site is part of a knee, an ankle, a foot, a shoulder, a hand, a wrist, an elbow, or a hip.

10. The method of claim 1, wherein the micronized allograft mixture is delivered to the microfracture site arthroscopically.

11. The method of claim 1, wherein a periosteal covering or a patch over the micronized allograft mixture is not used.

12. The method of claim 1, wherein the ratio of micronized cartilage mixture to platelet rich plasma is 1:1.

13. A method of articular cartilage repair, comprising the steps of:
    (a) placing a micronized cartilage mixture comprising (i) micronized allograft cartilage particles above 0 to about 300 microns, (ii) type II collagen, (iii) proteoglycans, (iv) cartilaginous growth factors into a first syringe, wherein the first syringe comprises a tube and a plunger that fits in the tube, the plunger being formed of a pushrod and a mixing element attached to the pushrod, the pushrod fitting into the mixing element and being designed to unsnap from the mixing element and snap back into the mixing element;
    (b) providing a second syringe or second container containing platelet rich plasma and injecting it into the first syringe;
    (c) removing the pushrod from the mixing element and moving the mixing element in at least one direction to mix the micronized allograft tissue particles with the platelet rich plasma to create a micronized allograft mixture with a paste consistency;
    (d) applying a needle or small cannula to the first syringe;
    (e) debriding an articular cartilage defect site to form a stable border;
    (f) forming several perforations in a subchondral bone plate at the base of the articular cartilage defect site using microfracture techniques to form a microfracture site;
    (g) applying a graft comprising the micronized allograft mixture with a paste consistency directly at the microfracture site without a covering over the articular cartilage defect site, such that the micronized allograft mixture fills the articular cartilage defect site, and
    (h) conforming the micronized allograft mixture to the size, shape, or both size and shape of the articular cartilage defect site.

14. The method of claim 13, wherein the micronized cartilage particles are obtained by dehydration of cartilage via desiccation.

15. The method of claim 14, wherein the ratio of micronized cartilage mixture to platelet rich plasma is 1:1.

16. The method of claim 13, wherein the micronized cartilage particles are obtained by dehydration of cartilage via desiccation or lyophilization.

17. The method of claim 13, further comprising the step of adding, to the micronized allograft mixture, a component selected from the group consisting of growth factors, antiseptics, antibiotics, electrolytes, and stem cells.

18. The method of claim 13, wherein the micronized allograft mixture further comprises bone marrow aspirate or bone marrow concentrate.

19. A method comprising:
    (a) placing a micronized cartilage mixture comprising (i) micronized allograft cartilage particles above 0 to about 300 microns, (ii) type II collagen, (iii) proteoglycans, (iv) cartilaginous growth factors into a first syringe, wherein the first syringe comprises a tube and a plunger that fits in the tube, the plunger being formed of a pushrod and a mixing element attached to the pushrod, the pushrod fitting into the mixing element and being designed to engage and disengage the mixing element;
    (b) providing a second syringe or second container containing platelet rich plasma and injecting the platelet rich plasma into the first syringe;
    (c) disengaging the pushrod from the mixing element to allow the mixing element to move in at least two different directions to allow mixing of the micronized allograft tissue particles with the platelet rich plasma to create a micronized allograft mixture with a paste consistency;
    (d) applying a needle or small cannula to the first syringe;
    (e) debriding an articular cartilage defect site to form a stable border;

(f) forming several perforations in a subchondral bone plate at the base of the articular cartilage defect site using microfracture techniques to form a microfracture site; and
(g) delivering a graft comprising the micronized allograft mixture with a paste consistency directly at the microfracture site, such that the micronized allograft mixture fills the articular cartilage defect site.

* * * * *